United States Patent
Seidl et al.

(10) Patent No.: US 6,673,969 B2
(45) Date of Patent: Jan. 6, 2004

(54) PROCESS FOR PREPARATION OF OXIMES AND RESULTING PRODUCTS

(75) Inventors: Peter R. Seidl, Rio de Janeiro (BR); Ángelo Da Cunha Pinto, Rio de Janeiro (BR); Arthur R. Menzel, Rio de Janeiro (BR); Roberto O. Portela Couto, Rio de Janeiro (BR)

(73) Assignee: Comselho Nacional de Desenvolvimento Cientifico e Tecnologico CNPQ, Brasilia (BR)

( * ) Notice: Subject to any disclaimer, the term of this patent is extended or adjusted under 35 U.S.C. 154(b) by 0 days.

(21) Appl. No.: 10/084,613

(22) Filed: Feb. 28, 2002

(65) Prior Publication Data

US 2002/0123650 A1 Sep. 5, 2002

Related U.S. Application Data

(63) Continuation-in-part of application No. 09/623,126, filed on Aug. 28, 2000, now abandoned.

(30) Foreign Application Priority Data

Feb. 27, 1998 (BR) .............................................. 9800783
Feb. 26, 1999 (WO) ................................ PCT/BR99/00020

(51) Int. Cl.[7] ...................... C07C 249/00; B01D 11/00; C01F 1/00
(52) U.S. Cl. ........................ 564/253; 564/265; 423/112
(58) Field of Search .................................. 564/253, 265; 423/112

(56) References Cited

U.S. PATENT DOCUMENTS

| | | | | |
|---|---|---|---|---|
| 3,967,956 A | * | 7/1976 | Payne | |
| 4,352,944 A | * | 10/1982 | Tyman et al. | |
| 4,697,038 A | * | 9/1987 | Tyman | |
| 4,865,824 A | * | 9/1989 | Pfuller | |
| 5,502,254 A | * | 3/1996 | Levin | |

* cited by examiner

*Primary Examiner*—Johann Richter
*Assistant Examiner*—Sikarl A. Witherspoon
(74) *Attorney, Agent, or Firm*—Morrison & Foerster LLP

(57) ABSTRACT

A new oxime mixture used as an extractant for metals, prepared from natural products containing alkylated phenols such as cashew nut shell liquid using mild reaction conditions, is expressed by the formula:

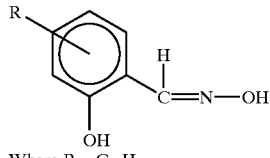

Where $R = C_{15}H_{31-n}$
$n = 0.2.4.6$

The oxime mixture is suitable for extracting gallium from waste effluents from ore processing, such as Bayer liquor.

11 Claims, No Drawings

PROCESS FOR PREPARATION OF OXIMES AND RESULTING PRODUCTS

REFERENCE TO RELATED APPLICATIONS

This application is a continuation-in-part of Ser. No. 09/623,126, filed Aug. 28, 2000, now abandoned. This application claims priority from International Application No. PCT/BR99/00020, filed Feb. 26, 1999, and Brazilian application No. PI 9800783-1, filed Feb. 27, 1998, the disclosures of which are incorporated by reference as if set forth fully herein.

BACKGROUND OF THE INVENTION

1. Field of the Invention

This invention relates to the preparation of novel compounds used for the recovery and purification of metals. More particularly, this invention relates to novel ortho alkenyl/alkyl substituted phenyl oxime compounds prepared from natural product sources and processes for selectively separating and recovering of metals from waste effluents and other such aqueous compositions and mixtures containing copper, gallium or other metal ions.

2. Description of the Related Art

The extraction of metals from minerals and their recovery from aqueous compositions and mixtures containing copper and other metals are important commercial processes.

Several extraction methods have been developed for recovering metals values. Solvent extraction processes for the recovery of metal values have certain well recognized advantages over other recovery methods, and such solvent extraction processes are increasing in number and types of applications.

Fundamental to a successful solvent extraction process for the recovery of metals is the identification of water immiscible composition (combination of compounds which will selectively bind to the metal and a suitable solvent) which will selectively extract the metal from an aqueous solution containing copper, and other metals. A further requirement for a successful metal recovery extraction techniques is an extracting composition having the property such that metal values extracted by the extracting solvent can be recovered from the same using another suitable aqueous phase.

Illustrative of such prior art solvent extraction processes are those described in U.S. Pat. No. 3,967,956 and in United Kingdom Patent No. 20 136 443. In the processes of these patents, palladium is recovered from a mixture of palladium and other platinum group metals through use of an extracting composition containing ortho hydroxy oxime compounds, such as alkyl substituted ortho-hydroxyphenyl oxime compounds. The extracted palladium metal is removed from the extracting solvent by contacting same with a strongly acidic aqueous solution.

This method is generally a useful procedure for recovering certain metals from the extracting solvent because the recovery procedure is pH dependent. With ortho- hydroxy phenyl oxime compounds, the extraction process is dependent on the ionizable nature of the phenolic hydrogen, and in the $Cu^{+2}$ system is generally believed to follow the following equilibrium in which "LH" is the un-ionized oxime:

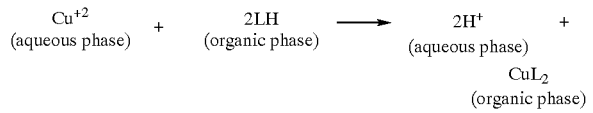

SUMMARY OF THE INVENTION

In accordance with this invention there is provided a small class of ortho alkenyl/alkyl substituted phenyloxime compounds which are useful in the extraction of copper, gallium and other metals. The compounds of this invention are of the formula:

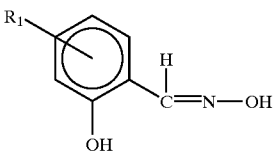

where $R_1=C_{15}H_{31-n}$ and $n=0,2,4,6$.

$R_1$ is a mixture of one alkyl and three alkenyl hydrocarbonic radical substitutes localized at the benzenic ring of the substituted phenyl aldoxime. That is, when $n=0$, $R_1$ is a substituent of the formula $C_{15}H_{31}$. When $n=2$, $R_1$ is an alkenyl substituent containing one double bond, represented by the following formula:

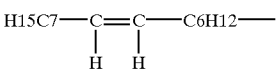

When $n=4$, $R_1$ is an alkenyl substituent containing two double bonds, represented by the following formula:

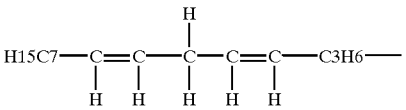

When $n=6$, $R_1$ is an alkenyl substituent containing three double bonds, represented by the following formula:

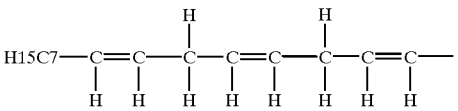

The invention uses mild reaction conditions so that the mixture of $R_1$ substituents referred to above can be made from the cardanol found in cashew nut shell liquid, which contains a mixture of molecules containing, no, one, two and three double bonds in the aliphatic lateral chain.

In addition to the aldehydes produced in accordance with the reaction scheme of this invention as precursors of aldoximes within the scope of this invention, ketones can be made by reacting anacardic acid with organolithium compounds like $CH_3Li$, $C_2H_5Li$, $C_3H_7Li$ and other such organometallic compounds, and then reacted like the aldehydes of this inventions to produce corresponding ketoximes.

Our invention is particularly directed to the extraction of gallium from waste effluents from the processing of aluminum-bearing ores, such as bauxite, in which gallium naturally occurs. The liquid effluent from factories that process bauxite to extract aluminum, commonly called Bayer liquor, contains gallium and other metals. Zinc minerals are also known to contain gallium and may be processed with the oximes of this invention for the extraction of gallium. The oximes of this invention also can be used to extract copper, nickel, silver, palladium, germanium and rare earth elements.

DETAILED DESCRIPTION OF THE INVENTION

The compounds of this invention are mixtures of the formula:

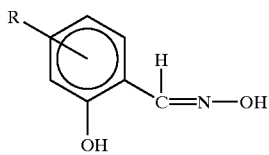

wherein $R_1$ is $C_{15}H_{31-n}$ and n is 0, 2, 4 or 6 as described above, and mixtures thereof.

The following compounds are illustrative of compounds within the purview of the generic formula set forth above, all of which can be conveniently prepared by simply selecting appropriate natural products for the use in procedures described here in below:

(2-hydroxy,3-alkyl)phenyl aldoxime;
(2-hydroxy,3-alkenyl)phenyl aldoxime;
(2-hydroxy,4-alkyl)phenyl aldoxime;
(2-hydroxy,4-alkenyl)phenyl aldoxime;
(2-hydroxy,5-alkyl)phenyl aldoxime;
(2-hydroxy,5-alkenyl)phenyl aldoxime;
(2-hydroxy,6-alkyl)phenyl aldoxime;
(2-hydroxy,6-alkenyl)phenyl aldoxime.

Particularly preferred are compounds of the above referenced generic formula in which n is 0 and $R_1$ is straight chain alkyl having 15 carbon atoms; n is 2 and $R_1$ is straight chain alkyl having 15 carbon atoms and one double bond between the 8- and 9-carbons; n is 4 and $R_1$ is straight chain alkyl having 15 carbon atoms and two double bonds between the 8- and 9-carbons and the 11- and 12-carbons 11 and 12; and n is 6 and $R_1$ is straight chain alkyl having 15 carbon atoms and three double bonds between the 8- and 9-carbons, the 11-and 12-carbons and the 14- and 15-carbons.

The compounds of this invention can be conveniently prepared by a variety of methods. One preferred method for preparing the compounds of this invention is illustrated in the following Reaction Scheme A:

Reaction Scheme A

Carbonylation

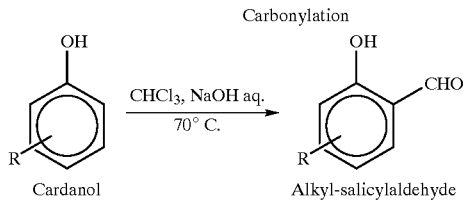

Where R = $C_{15}H_{31-n}$
n = 0,2,4,6

Oximation

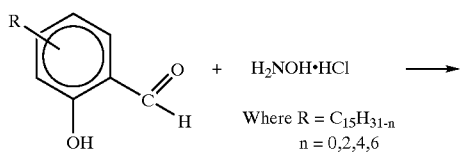

Where R = $C_{15}H_{31-n}$
n = 0,2,4,6

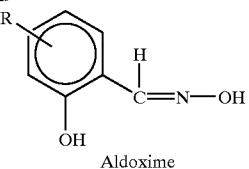

Aldoxime

Cashew nut shell liquid natural alkylated phenols are used as starting materials to obtain aldehyde intermediates are submitted to reaction with hydroxylamine to produce corresponding aldoximes.

It is known that cardanol is present in cashew nut shell liquid, in concentrations of 5 to 10%, weight by weight, as mentioned in the literature. On the other hand, it is also known that heating cashew nut shell liquid between 180 to 200° C., promotes the decarboxylation of anacardic acid, its main component, transforming it into cardanol. Fractional distillation under reduced pressure, at temperature of 200° C. and 10–25 mm Hg, produces cardanol in yields up to 65% in weight, relative to the cashew nut shell liquid. This cardanol is a mixture of saturated cardanol and unsaturated cardanols as disclosed above.

On the laboratory scale, cashew nut shell liquid was distilled under reduced pressure (10–25 mm Hg), at temperatures in the range of 200 to 230° C. In a round bottom glass flask reaction with three necks, adapted to a refluxer condenser, addition funnels with pressure equalizer and magnetic stirrer, were added, under an inert atmosphere ($N_2$), 45 g of chloroform and 100 g of cardanol mixture distilled from cashew nut shell liquid. The system was heated and 300 mL of a 4.6N sodium hydroxide solution was added drop by drop, keeping on stirring and refluxing for six hours and thirty minutes, at 65° C. After reaction, the system is allowed to cool at room temperature.

Pure hydrochloric acid was added to the reaction mixture until a pH of 1 was reached. The purpose of this reduction in pH is to improve the yield of the reaction, transforming the by-product acetals in salicylaldehyde, and also promoting a good separation of organic and aqueous phases.

The organic layer was separated from the aqueous layer by simple decantation, using a separating funnel. 25 g of hydroxylamine hydrochloride dissolved in 50 mL of water was added to the organic layer, keeping the system at 65° C. under agitation, for three hours and thirty minutes. The organic layer was separated from the aqueous layer by decantation. The product was purified by extraction with isopropyl ether and concentrated by evaporation of the solvent. These reaction conditions are such as not to reduce the oximes produced from the mixture of cardanols of this invention to a single oxime, but instead produce a mixture of oximes, either aldoximes or ketoximes as desired, that corresponds to the mixture of cardanols isolated from the natural cashew nut shell liquid.

The complexation capacity of this new extractant, can be exemplified by starting from a solution of copper sulphate of known concentration, a reaction with the oximes was carried on; immediately after reaction, the copper remaining in solution is measured by titration.

The procedure is as follows: Weigh 1 g of oximes. Solubilize them totally, using as small a volume of amyl alcohol as possible. In a separating funnel, add 18 ml of $CuSO_4$ (5 g/L) and mix thoroughly. Let the layers separate and discard the aqueous layer. To the organic layer which contains the extractant and the extracted $Cu^{2+}$, add 14.0 mL of $H_2SO_4$, 1:4 v/v to extract the $Cu^{2+}$ back to the aqueous phase.

The aqueous layer is transferred to a beaker, deonized water is added (approximately 50 mL) and the solution is neutralized with concentrated $NH_4OH$ and an excess is added to solubilize all of the $Cu^{2+}$ as cupric amino complex. After this, the solution is transferred to a glass graduated cylinder and the final volume is reported. A sample of 10.0 mL is transferred to an Erlenmeyer flask and the $Cu^{+2}$ is titrated with standard 0.001N EDTA solution, using murexide as indicator.

During the experimental trials, it was noticed that during of the carbonylation reaction of the cardanol mixture, using the classic Reimer-Tiemann reaction, very often emulsions were formed during the addition of the solution of NaOH to the reaction medium constituted of chloroform and cashew nut shell liquid.

It was also considered that the double bonds of the alkenyl substituents present in the mixture of the oximes obtained were probably the sites where the hydration reaction could be carried on simultaneously with carbonylation of the benzenic ring.

To solve the problem of emulsion formation, the double bonds were saturated by hydrogenation of the cashew nut shell liquid before reaction. The aim was to eliminate or reduce the possibility of emulsion formation.

Alternatively, the compounds of the invention can be prepared by a variation of the procedure of Reaction Scheme A, which is depicted in Reaction Scheme B:

Reaction Scheme B

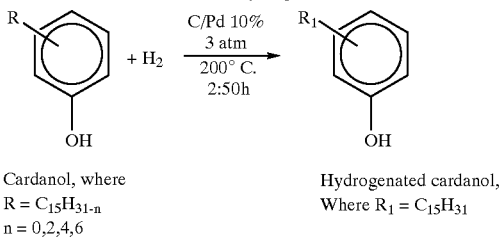

Cardanol, where
$R = C_{15}H_{31-n}$
$n = 0,2,4,6$

Hydrogenated cardanol,
Where $R_1 = C_{15}H_{31}$

After the hydrogenation reaction, the catalyst C/Pd was filtered using diatomite powder to clarify the product. The filtration was conducted in Buchner, under reduced pressure at temperature in the range of 40–45° C. The hydrogenated cardanol after cooling down to room temperature, becomes solid around 28–30° C., in agreement with the literature.

The product was characterized as a hydrogenated cardanol by its Refraction Index and by Infrared spectroscopy.

During the trials it was observed that the occurrence of emulsions was greatly reduced, making the operating tasks easier.

After the reactions, according to Scheme B, there were carried on the same reactions of carbonylation and oximation as per the following Scheme A:

Reimer-Tiemann Reaction

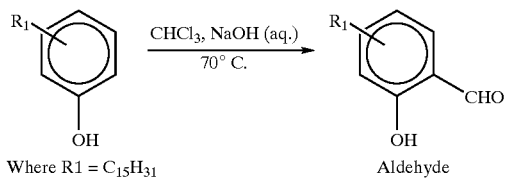

Where $R1 = C_{15}H_{31}$

Oximation Reaction

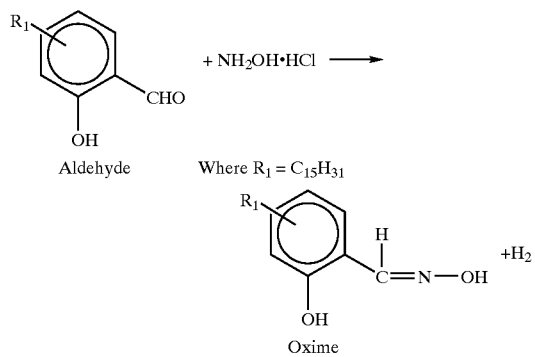

Aldehyde           Where $R_1 = C_{15}H_{31}$

Oxime

The hydrogenation reaction was carried on in a Parr reactor, setting the operational conditions as following: temperature 200° C., time 2 hours 50 minutes, speed of mechanical stirrer in the range of 800–1200 rpm. The aldoxime obtained was evaluated as for its capacity of complexing $Cu^{+2}$, using the same method as used for the mixture of oximes produced as per Scheme A.

The process of Reaction Schemes A and B can be conducted in a batch fashion. The reactants and reagents may be initially introduced into the reaction zone batchwise and either intermittently or continuously into the reaction zone during the course of the reaction. The addition of NaOH solution into the reaction vessel during the Reimer-Tiemann reaction is an example of this procedure.

The following specific examples are presented to more particularly illustrate the invention.

EXAMPLE 1

1. Cashew Nut Shell Liquid Pre-treatment.

100 g of cashew nut shell liquid was introduced into a distillation rounded bottom glass vessel to which were adapted a condenser and a thermometer at the top and a receiving glass at the end of the condenser. The apparatus were linked to the vacuum line of the laboratory and the distillation vessel was supported by an electric mantle. Under vacuum of 10–25 mm Hg, heating was started and increasing slowly until the temperature at the top of the vessel reach 180° C., when a mist of the $CO_2$ starts to condense. At this temperature it takes about 45 minutes to remove all $CO_2$ by the vacuum system. The temperature at the top of distillation vessel then rises to 200–230° C., where the first fraction was condensed. This first fraction was discarded, after stopping the vacuum system and the heater. Upon restarting the operation, when the temperature of vapor at the top the distillation vessel reaches 200–230° C., a mild yellow liquid starts to condense.

This liquid takes about two hours to be distilled, and the temperature rises again to 250–280° C., when a red liquid starts to condense.

The yellow fraction was separated and characterized by refractive index and infrared spectroscopy. By comparison with data in the literature, it was identified as cardanol.

2. Reimer-Tiemann Reaction

In a rounded bottom glass vessel with three openings, adapted to a refluxing condenser, addition funnel with pressure equalization and provided with magnetic stirrer, were added at inert atmosphere ($N_2$), 45.0 g of chloroform and 100 g of cardanol, just after distillation. The system was heated up to 60° C. and 300 mL of 4.6N sodium hydroxide solution was added drop by drop, keeping in reflux for six hours and thirty minutes at 70–75° C.

The organic phase was separated from the aqueous phase.

3. Oximation Reaction

To the organic phase separated in the Reimer Tiemann reaction step, 25.0 g of hydroxylamine chloride were added, keeping the system at 75° C. for three hours and thirty minutes. The organic layer was separated of the aqueous layer by simple decantation.

EXAMPLE 2

1. Cashew Nut Shell Liquid Pre-treatment.

150 g of cashew nut shell liquid was introduced into a distillation rounded bottom glass vessel to which were adapted a condenser and a thermometer at the top and a receiving glass at the end of the condenser. The apparatus were linked to the vacuum line of the laboratory and the distillation vessel was supported by an electric mantle. Under vacuum of 5 to 10 mm Hg, heating was started and increasing slowly until the temperature at the top of the vessel reached 180° C., when mist of $CO_2$ started to condense. At this temperature it takes about 30 minutes to remove all $CO_2$ by the vacuum system. The temperature at the top of distillation vessel then rose to 200–230° C., where the first fraction was condensed. This first fraction was discarded and the operation was restarted, and when the temperature of the vapor at the top of distillation vessel reached 200–230° C., a mild yellow liquid started to condense.

This liquid took about two hours and thirty minutes to be distilled and the temperature rose again to 250–280° C., when a red liquid started to condense.

The yellow fraction was separated and characterized by refractive index and infrared spectroscopy, which by comparison with data in the literature, was identified as cardanol.

2. Reimer-Tiemann Reaction

In a rounded bottom glass vessel, adapted to a refluxing condenser, addition funnel and provided with mechanical stirrer, 50 g of chloroform and 100 g of cardanol were added just after distillation. The system was heated up to 65° C. and 300 mL of 4.6N sodium hydroxide solution was added drop by drop, keeping in reflux for nine hours at 65–75° C.

The organic phase was separated from the aqueous phase.

3. Oximation Reaction

To the organic phase separated in the Reimer-Tiemann reaction step, were added 30 g of hydroxylamine hydrochloride, keeping the system at 70° C. for four hours. The organic layer was separated of the aqueous layer by simple decantation.

EXAMPLE 3

1. Cashew Nut Shell Liquid Pre-treatment 120 g of cashew nut shell liquid was introduced into a distillation rounded bottom glass vessel to which were adapted a condenser, thermometer and receiving flask. The system was linked to a vacuum line and heated by electric mantle. Under a vacuum of 5–10 mmHg, heating was started and increased until the temperature at top of the distillation vessel reached 180° C., when a mist of $CO_2$ started to condense. At this temperature it takes about 35 minutes to remove all $CO_2$ by the vacuum system. When the temperature at the top of distillation vessel rose to 200–230° C., the first fraction was condensed. This fraction was discarded. Re-starting the operation, a mild yellow liquid started to condense, at 200–230° C.

This liquid took about one hour and forty minutes to complete distillation and the temperature rose again to 250–280° C., when a red liquid started to condense.

The yellow fraction was separated and characterized by refractive index and infrared spectroscopy. By comparison with data in the literature, it was identified as cardanol.

2. Hydrogenation of Cashew Nut Shell Liquid 150 mL of cardanol immediately after distillation was placed in a Parr reactor where 2.32 g of Degussa Catalyst C/Pd 10% were previously poured. The reactor was closed and the valve of $H_2$ was opened, setting the pressure at 3 atm. (44 psi) and the heater was switched on increasing the temperature gradually. Agitation was fixed at a range of 800–850 rpm until it reached 200° C. Up to 2 hours after reaching 200° C., the speed was kept at 800 rpm. 2 hours after the reaction started (considered when 200° C. was reached) and until 2 hours 50 minutes, the agitation was increased to the range of 900–1200 rpm. The reaction was stopped at this moment. The hydrogen valve was closed and the mixture allowed to cool a room temperature.

The reaction mixture was transferred to a Buchner funnel linked to the vacuum system of the laboratory. An excess of diatomite powder was added to the reaction mixture, stirred with a glass rod and filtered slowly. This procedure was carried out at 45° C. The filtered cardanol was clarified to a yellow to brown color and poured into a stoppered glass. After cooling to room temperature it solidified, taking on a waxy appearance.

3. Reimer-Tiemann Reaction

In a rounded bottom glass vessel with three openings, adapted to addition funnel with pressure equalization and provided with mechanical stirrer and condenser, were added 50.0 g of chloroform and 110 g of cardanol, just after distillation. The system was heated up to 70° C. and a 4.6N sodium hydroxide solution was added drop by drop, keeping in reflux for seven hours at 60–70° C.

The organic phase was separated from the aqueous phase.

To the organic phase separated in the Reimer Tiemann reaction step, were added 30 g of hydroxylamine hydrochloride, keeping the system at 65–70° C. for five hours. The organic layer was separated of the aqueous layer by simple decantation.

Characterization

Aldoximes were characterized by Infrared Spectroscopy and Nuclear Magnetic Resonance (NMR), in the procedures explained in Scheme A, and by Infrared Spectroscopy in Scheme B.

The results are as follows:

Scheme A:
  Oxime: IR: 1550.0–1714.3 $cm^{-1}$, stretching vibration typical of bond C=N NMR ($CDCl_3$): d 6,4–7,4 (3H), 0,6–2,8 (6H)

Scheme B:
  Oxime: IR: 1550–1650 $cm^{-1}$, stretching vibration typical of bond C=N Extraction of Copper

EXAMPLE 1

(Scheme A)

1 g of oxime from trial number 4 was quantitatively transferred to a beaker and solubilized with as small a volume of amyl alcohol as possible. In a separating funnel, 18 mL of $CuSO_4$ (5 g/L) were added and mixed thoroughly. The layers were allowed to separate and the aqueous layer was discarded. To the organic layer which contains the extractant and the extracted Cu2+, 14.0 ml $H_2SO_4$, 1:4 v/v, were added to extract the $Cu^{2+}$ back to the aqueous phase.

The aqueous layer was transferred to a beaker, deionized water was added (approximately 50 mL) and the solution was neutralized with concentrated $NH_4OH$ and an excess was added to solubilize all $Cu^{2+}$ as cupric amino complex. After this, the solution was transferred to a glass graduated cylinder and the final volume was reported. A sample of 10.0 mL was put in an Erlenmeyer flask and the $Cu^{+2}$ was titrated with standard EDTA 0.001N solution, using murexide as indicator. Extraction gave 49.3 mg $Cu^{+2}$/g oxime.

The result, after calculations was 49,3 mg $Cu^{+2}$/g oxime.

EXAMPLE 2

(Scheme B)

1 g of oxime from trial number 23 was quantitatively transferred to a beaker and solubilized with the smaller volume of amyl alcohol as possible. In a separating funnel, add 18 mL of $CuSO_4$(5 g/L) and mix thoroughly. The layers were allowed to separate and the aqueous layer was discarded. To the organic layer which contains the extractant and the extracted $Cu^{2+}$ was added 14.0 mL of $H_2SO_4$, 1.4 v/v, to extract the $Cu^{2+}$ back to the aqueous phase.

The aqueous layer was transferred to a beaker, deionized water was added (approximately 50 mL) and the solution is neutralized with concentrated $NH_4OH$ and an excess was added to solubilize all Cu2+ as cupric amino complex. After this, the solution was transferred to a glass graduated cylinder and the final volume was reported. A sample of 10.0 mL was put in an Erlenmeyer flask and the $Cu^{+2}$ was titrated with standard 0.001N EDTA solution, using murexide as indicator. Extraction gave 49.6 mg $Cu^{+2}$/g oxime.

Extraction of Gallium

To an amount of Bayer liquor containing a known concentration of gallium is added an aqueous suspension of the oximes of this invention. The mixture is heated and stirred to produce a complex of the oximes with the gallium in the Bayer liquor. A strong acid such as hydrochloric or sulfuric is added to the complexed mixture to liberate the gallium ions from the complex, and the gallium is isolated from the liberated extract and smelted to produce gallium metal.

What is claimed is:

1. A process for preparing an aqueous suspension of oximes, comprising:
   preparing a mixture of alkyl-salicyl-aldehydes of allyl phenols by reacting cardanol with an aqueous solution of sodium hydroxide in a temperature range of 20 to 75° C., using chloroform as reagent and solvent;
   preparing a mixture of aldoxime or ketoxime by reacting the mixture of alkyl-salicyl-aldehydes or a mixture of alkyl-salicyl-ketones derived from the mixture of alkyl-salicyl-aldehydes with hydroxylamine sulfate, hydroxylamine hydrochloride or other salt of hydroxylamine; and
   adding the oximes to an aqueous solution to produce an aqueous suspension of oximes.

2. The process of claim 1, wherein the cardanol is derived from cashew nut shell liquid.

3. The process of claim 1, wherein the cardanol is unsaturated.

4. An aqueous suspension produced by the process of claim 1, wherein the aqueous suspension comprises a mixture of oximes expressed by the formula:

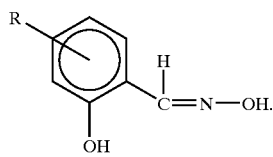

Where $R = C_{15}H_{31-n}$
n = 0.2.4.6

5. A process for preparing an oxime mixture of the formula:

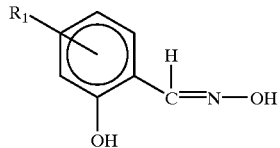

where $R=C_{15}H_{31}$, comprising:
   (a) preparing an alkyl-salicyl-aldehyde of cardanol by reacting a solution of cardanol in chloroform with an aqueous solution of sodium hydroxide at a temperature of 20 to 70° C.;
   (b) reacting the alkyl-salicyl-aldehyde of cardanol prepared in step (a) with a hydroxylamine salt to produce an oxime of said formula; and
   (c) suspending the oxime in an aqueous solution.

6. The process of claim 5, wherein the hydroxylamine salt is hydroxylamine sulfate or hydroxylamine hydrochloride.

7. The process of claim 2, further comprising:
   heating the cashew nut shell liquid to a temperature between 180 to 200° C. to promote transformation of anacardic acid into cardanol; and
   fractionally distilling the heated cashew nut shell liquor at a pressure of 10–25 mm Hg to produce directly a substantially pure mixture of saturated cardanol and unsaturated cardanols.

8. A process for the extraction of gallium from an effluent containing gallium, comprising:
   adding an aqueous suspension of an oxime mixture expressed by the formula:

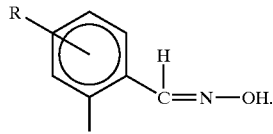

Where $R = C_{15}H_{31-n}$
n = 0.2.4.6 to the effluent containing gallium to produce a complex containing gallium,
   adding a strong acid to the complex to produce a gallium-contain g mixture, and
   isolating gallium from the gallium-containing mixture.

9. The process of claim 8, wherein the effluent containing gallium is aqueous.

10. The process of claim 8, wherein the effluent is Bayer liquor.

11. The process of claim 8, wherein the strong acid is hydrochloric acid or sulfuric acid.

* * * * *

UNITED STATES PATENT AND TRADEMARK OFFICE
CERTIFICATE OF CORRECTION

PATENT NO. : 6,673,969 B2
DATED : January 6, 2004
INVENTOR(S) : Peter R. Seidel et al.

It is certified that error appears in the above-identified patent and that said Letters Patent is hereby corrected as shown below:

<u>Title page,</u>
Item [73], should read:

-- [73] Assignee: Conselho Nacional De Desenvolvimento Cientifico E Tecnologico CNPQ, Braslia, Brazil --

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,673,969 B2
DATED         : January 6, 2004
INVENTOR(S)   : Peter R. Seidel et al.

It is certified that error appears in the above-identified patent and that said Letters Patent is hereby corrected as shown below:

Title page,
Item [73], should read:

-- [73] Assignee: Conselho Nacional De Desenvolvimento Cientifico E. Tecnologico CNPQ, Brasilia, Brazil --

This certificate supersedes Certificate of Correction issued March 30, 2004.

Signed and Sealed this

Tenth Day of August, 2004

JON W. DUDAS
*Acting Director of the United States Patent and Trademark Office*